United States Patent
West et al.

(10) Patent No.: US 7,329,254 B2
(45) Date of Patent: Feb. 12, 2008

(54) SYSTEMS AND METHODS FOR TREATING DYSFUNCTIONS IN THE INTESTINES AND RECTUM THAT ADAPT TO THE ANATOMIC FORM AND STRUCTURE OF DIFFERENT INDIVIDUALS

(75) Inventors: Scott West, Livermore, CA (US); John W. Gaiser, Mountain View, CA (US); Patrick Rimroth, San Jose, CA (US); Larry C. Heaton, Pleasanton, CA (US)

(73) Assignee: Curon Medical, Inc., Hercules, CA (US)

( * ) Notice: Subject to any disclaimer, the term of this patent is extended or adjusted under 35 U.S.C. 154(b) by 216 days.

(21) Appl. No.: 10/911,395

(22) Filed: Aug. 4, 2004

(65) Prior Publication Data

US 2005/0228371 A1    Oct. 13, 2005

Related U.S. Application Data

(60) Continuation-in-part of application No. 10/674,242, filed on Sep. 29, 2003, now Pat. No. 7,056,320, which is a division of application No. 09/556,169, filed on Apr. 21, 2000, now Pat. No. 6,645,201, and a continuation-in-part of application No. 09/026,296, filed on Feb. 19, 1998, now Pat. No. 6,009,877.

(60) Provisional application No. 60/143,749, filed on Jul. 14, 1999.

(51) Int. Cl.
 *A61B 18/18* (2006.01)
(52) U.S. Cl. ........................................... 606/41

(58) Field of Classification Search .................. 606/41, 606/27–52; 607/138
See application file for complete search history.

(56) References Cited

U.S. PATENT DOCUMENTS

| | | | |
|---|---|---|---|
| 2,382,109 A | | 8/1945 | Sheiffele |
| 5,370,675 A | | 12/1994 | Edwards et al. |
| 5,403,311 A | | 4/1995 | Abele et al. |
| 5,451,223 A | | 9/1995 | Ben-Simhon |
| 5,582,611 A | * | 12/1996 | Tsuruta et al. ................ 606/46 |
| 5,709,224 A | | 1/1998 | Behl et al. |
| 5,827,276 A | | 10/1998 | LeVeen et al. |
| 5,849,011 A | | 12/1998 | Jones et al. |
| 5,873,877 A | | 2/1999 | McGaffigan et al. |
| 6,009,877 A | | 1/2000 | Edwards |
| 6,014,589 A | | 1/2000 | Farley et al. |

(Continued)

FOREIGN PATENT DOCUMENTS

WO     WO 9811834     3/1998

(Continued)

*Primary Examiner*—Roy D. Gibson
*Assistant Examiner*—Pete Vrettakos
(74) *Attorney, Agent, or Firm*—Ryan Kromholz and Manion S.C.

(57) ABSTRACT

An assembly for treating tissue in the anal canal uses a barrel structure having a dimension that can be selectively altered to be conducive for insertion into an anal canal according to an anatomic condition assessed within the anal canal. An electrode is carried by the barrel structure that can be coupled to a source of tissue ablation energy, which, when applied through the electrode, forms a lesion.

3 Claims, 14 Drawing Sheets

U.S. PATENT DOCUMENTS

| | | |
|---|---|---|
| 6,017,338 A | 1/2000 | Brucker et al. |
| 6,056,744 A | 5/2000 | Edwards |
| 6,092,528 A | 7/2000 | Edwards |
| 6,231,571 B1 | 5/2001 | Ellman et al. |
| 6,325,798 B1 | 12/2001 | Edwards et al. |
| 6,419,673 B1 * | 7/2002 | Edwards et al. ............... 606/41 |
| 6,645,201 B1 * | 11/2003 | Utley et al. .................... 606/41 |
| 7,056,320 B2 * | 6/2006 | Utley et al. .................... 606/41 |

FOREIGN PATENT DOCUMENTS

| WO | WO 0059393 | 10/2000 |
|---|---|---|

\* cited by examiner

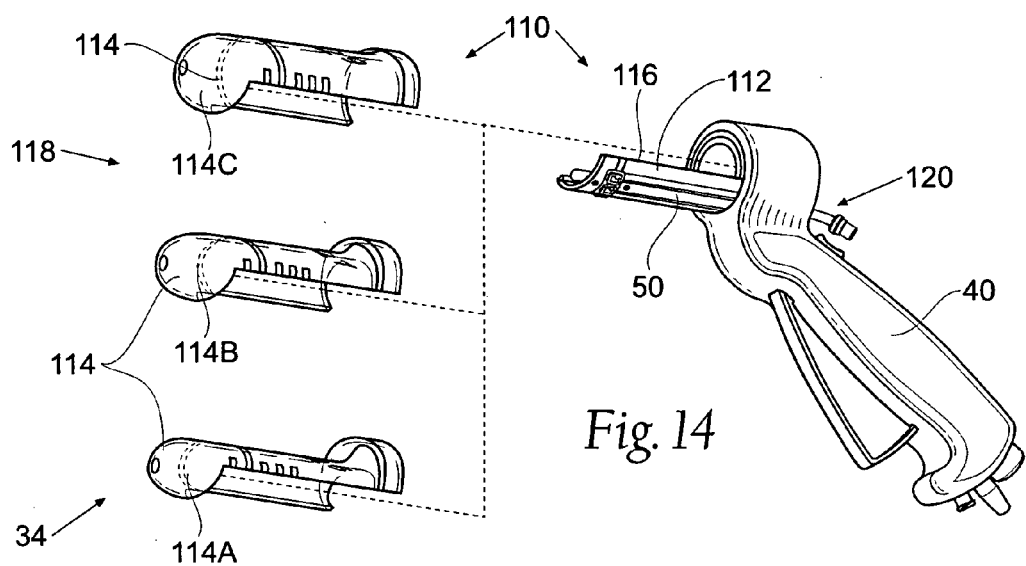
*Fig. 14*
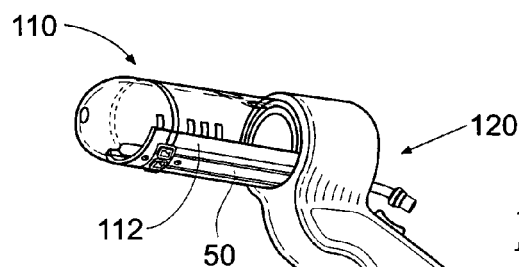
*Fig. 15*
*Fig. 16*
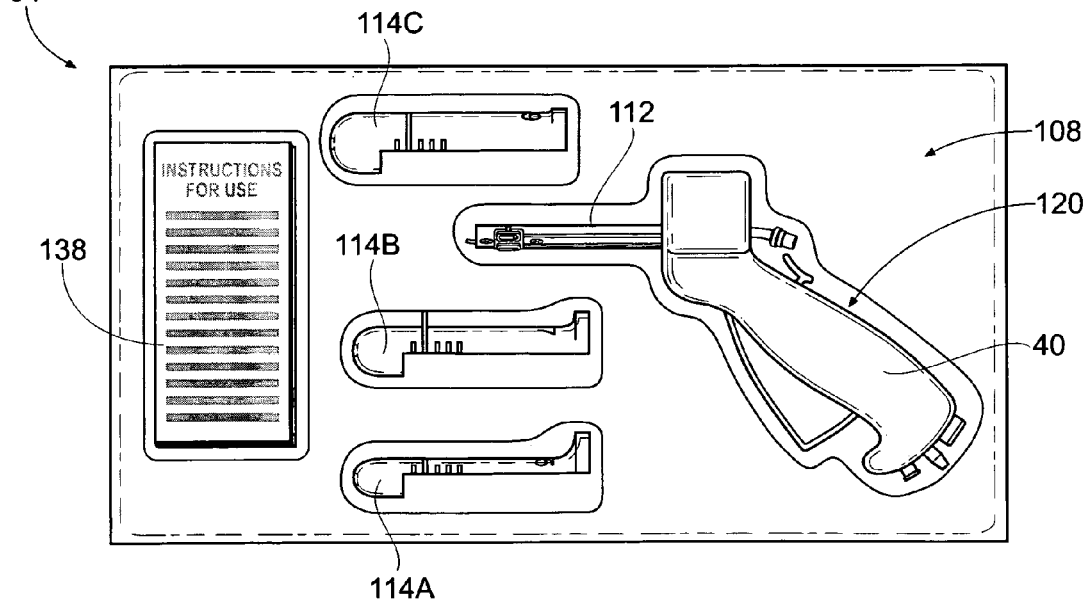

SYSTEMS AND METHODS FOR TREATING DYSFUNCTIONS IN THE INTESTINES AND RECTUM THAT ADAPT TO THE ANATOMIC FORM AND STRUCTURE OF DIFFERENT INDIVIDUALS

RELATED APPLICATIONS

This application is a continuation-in-part of U.S. patent application Ser. No. 10/674,242, filed Sep. 29, 2003, and entitled "Systems and Methods for Treating Dysfunctions in the Intestines and Rectum" (now U.S. Pat. No. 7,056,320), which is a divisional of U.S. patent application Ser. No. 09/556,169, filed Apr. 21, 2000 (now U.S. Pat. No. 6,645,201), which claims the benefit of U.S. Provisional Patent Application Ser. No. 60/143,749, filed Jul. 14, 1999, and entitled "Systems and Methods for Treating Dysfunctions in the Intestines and Rectum," which are incorporated herein by reference, and which is also a continuation-in-part of U.S. patent application Ser. No. 09/026,296, filed Feb. 19, 1998 (now U.S. Pat. No. 6,009,877), and entitled "Method for Treating Sphincter," which is also incorporated herein by reference.

FIELD OF THE INVENTION

In a general sense, the invention is directed to systems and methods for treating interior tissue regions of the body. More specifically, the invention is directed to systems and methods for treating dysfunction in the intestines and rectum.

BACKGROUND OF THE INVENTION

The gastrointestinal tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from another region of the alimentary canal.

In the rectum, two muscular rings, called the internal and external sphincter muscles, normally keep fecal material from leaving the anal canal. The external sphincter muscle is a voluntary muscle, and the internal sphincter muscle is an involuntary muscle. Together, by voluntary and involuntary action, these muscles normally contract to keep fecal material in the anal canal.

The rectum can stretch and hold fecal material for some time after a person becomes aware that the material is there. The holding action of these sphincter muscles is critical in maintaining fecal continence.

Damage to the external or internal sphincter muscles can cause these sphincters to dysfunction or otherwise lose their tone, such that they can no longer sustain the essential fecal holding action. Fecal incontinence results, as fecal material can descend through the anal canal without warning, stimulating the sudden urge to defecate.

The recurring sensation of uncontrolled fecal urgency alone can produce significant, negative impact on lifestyle. The physical effects of fecal incontinence (i.e., the loss of normal control of the bowels and gas, liquid, and solid stool leakage from the rectum at unexpected times) can also cause embarrassment, shame, and a loss of confidence, and can further lead to mental depression.

Fecal incontinence affects as many as one million Americans. It is more common in women and in the elderly of both sexes. Many people with fecal incontinence are ashamed to talk about their problem with their doctor or family.

In women, damage to the external or internal sphincter muscle can occur during childbirth. It is especially likely to happen in a difficult delivery that uses forceps and/or an episiotomy. Muscle damage can also occur as a result of trauma, or during rectal surgery. It may also occur in people with inflammatory bowel disease or an abscess in the perirectal area.

Young people suffering damage to these sphincters in the rectum can often compensate for the muscle weakness to avoid incontinence. However, they typically develop incontinence in later life, as their muscles grow weaker and the supporting structures in the pelvis become loose.

There are non-surgical ways to treat fecal incontinence. For example, dietary bulking agents or other antimotility agents (like fats) can be used to change the texture of fecal material, to slow its descent through the rectum. Biofeedback therapy has met with success. Still, this therapy is time consuming and works to overcome dysfunction only of the voluntary external sphincter muscle. Biofeedback therapy is not effective in overcoming dysfunction of the involuntary internal sphincter muscle.

There are also various surgical options for treating fecal incontinence. These surgical options include, for example, Parks post-anal repair, encirclement (using Tiersch wire or gracilis muscle), overlapping sphincteroplasty and levatoroplasty, gluteus muscle transposition, colostomy, gracilis muscle stimulated neosphinter, and artificial bowel sphincters.

Other abnormal, uncomfortable or debilitating conditions can occur in the rectum and adjoining intestines, which require treatment or surgical intervention. For example, cancer often arises in polyps, small noncancerous growths in the intestine. A tendency to develop polyps is probably influenced by genes. Regardless, it is a common practice to remove polyps, when discovered.

Many people also suffer hemorrhoids, or piles. Hemorrhoids are enlargements of the veins of the rectum. Many people seem to inherit a tendency toward developing hemorrhoids. However, any condition that causes prolonged or repeated increases in the blood pressure in the rectal veins may contribute to the development of hemorrhoids. Such conditions include constipation, pregnancy, and long periods of standing. Hemorrhoids can be internal (protruding through the anal sphincter) or external (covered with skin outside the sphincter). Hemorrhoids of the external veins usually cause little discomfort, unless a blood clot forms in the affected vein and results in inflammation. Hemorrhoids of the internal veins may bleed or descend through the anus as a result of bowel movements. Such hemorrhoids may cause pain or itching. Mild cases can be treated with medicated ointments or suppositories (inserted capsules), or by soaking in warm water. If the victim repeatedly suffers painful attacks or bleeding, a physician may remove the hemorrhoids surgically. However, surgery for hemorrhoids can itself damage the external or internal sphincter muscle and lead to fecal incontinence.

SUMMARY OF THE INVENTION

The invention provides improved systems and methods of systems and methods for treating dysfunctions in the intestines, rectum and anal canal.

One aspect of the invention provides an assembly for treating tissue in the anal canal. The assembly includes a barrel structure having a dimension that can be selectively altered according to an anatomic condition assessed within the anal canal, to be conducive for insertion into an anal canal. An electrode is carried by the barrel structure that can be coupled to a source of tissue ablation energy, which, when applied through the electrode, forms a lesion.

In one embodiment, the dimension of the barrel structure is altered by selecting a barrel structure from a family comprising at least two barrel structures each having a different dimension.

In one embodiment, the barrel structure includes a frame component and a canopy component sized and configured to be attached to the frame component. In this embodiment, the dimension of the barrel structure is altered by selecting from a family comprising at least two canopy components each having a different dimension.

In one embodiment, the barrel structure includes an upper jaw component and a lower jaw component. In this embodiment, the dimension of the barrel structure is altered by articulating the upper jaw component with respect to the lower jaw component about a pivot point mount.

Another aspect of the invention provides a method for forming a lesion in a tissue region at or near a sphincter in the anal canal of an individual. The method provides a barrel structure carrying an electrode sized and configured to be coupled to a source of tissue ablation energy to be applied through the electrode to form a lesion. The method assesses the anatomic requirements of the individual in the region of the anal canal and selects a dimension for the barrel structure conducive for advancement into the anal canal based upon the assessment. The method inserts the barrel structure at the selected dimension into the anal cavity with the electrode retracted within the barrel structure, and visualizes through the barrel structure to align the electrode in a desired location with respect to the dentate line. The method advances the electrode to penetrate tissue at or near a sphincter, and applies energy through the electrode to create a lesion in the sphincter.

Features and advantages of the inventions are set forth in the following Description and Drawings.

BRIEF DESCRIPTION OF THE DRAWINGS

FIG. 14 shows another representative embodiment of a family of treatment devices for treating sphincters and adjoining tissue regions in the rectum and anal canal, the family comprising a universal handle with a composite barrel assembly that engages an assortment of canopy components of different dimensions that are configured to adapt to the anatomic form and structure of different individuals in these tissue regions.

FIG. 15 is a perspective view of the universal handle shown in FIG. 14 with a canopy component of a selected dimension engaged.

FIG. 16 is a kit containing the family of treatment devices shown in FIG. 14, together with instructions for use.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction of sphincters and adjoining tissue regions in the body. The systems and methods are particularly well suited for treating these dysfunctions in the lower gastrointestinal tract, e.g., in the intestines, rectum and anal canal. For this reason, the systems and methods will be described in this context.

Still, it should be appreciated that the disclosed systems and methods are applicable for use in treating other dysfunctions elsewhere in the body, e.g., for restoring compliance to or otherwise tightening interior tissue or muscle regions. The systems and methods that embody features of the invention are also adaptable for use with systems and surgical techniques that are not necessarily catheter based.

I. Anatomy of the Rectum and Anal Canal

Figure 1:
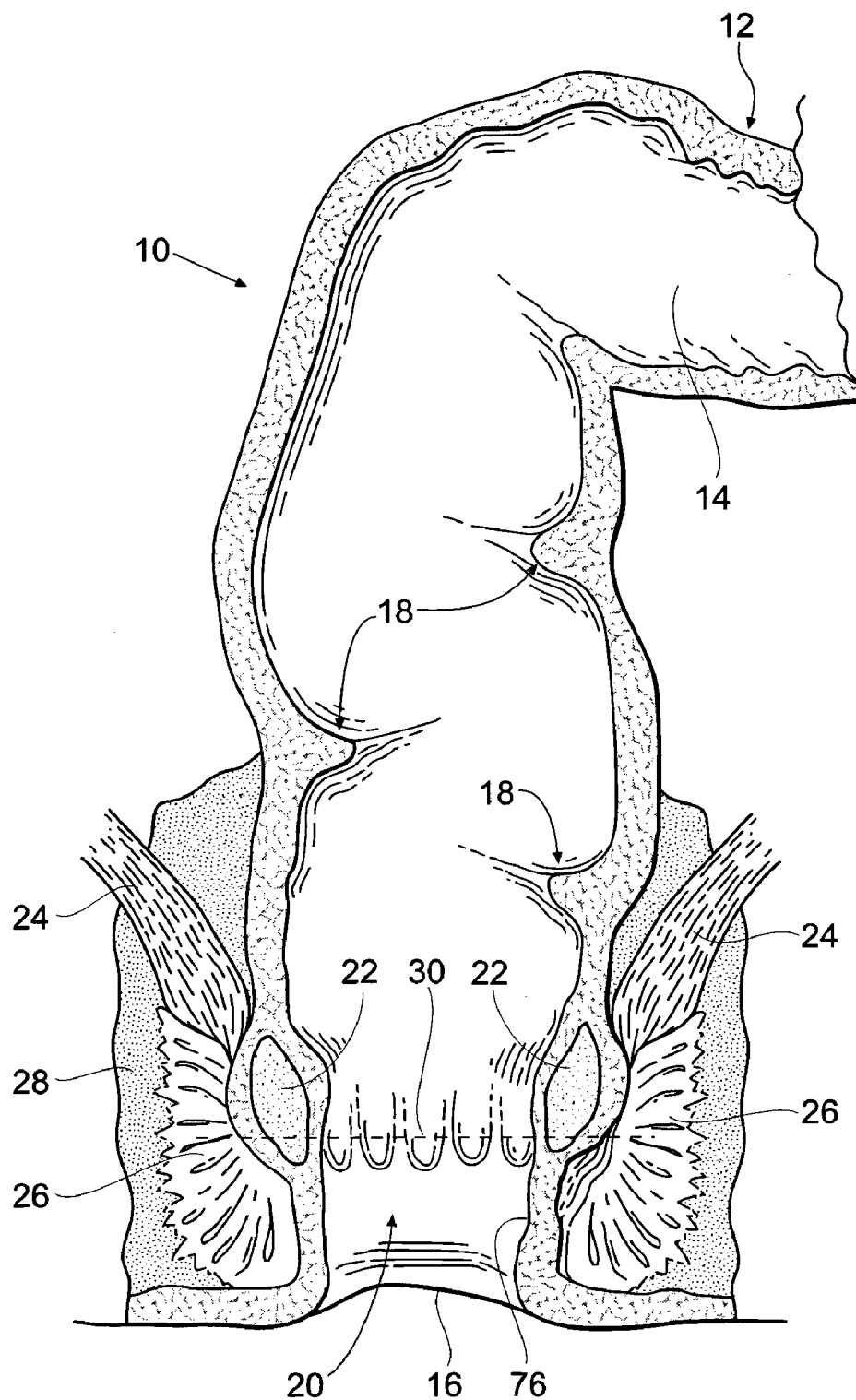
FIG. 1 is an anatomic view of the rectum and anal canal.

As FIG. 1 shows, the rectum is the terminal part of the large intestine 12. The rectum 10 extends from the sigmoid flexure 14 (which is the narrowest part of the colon) to the anal orifice 16. The rectum 10 is about 15 to 17 cm in overall length.

The upper or superior portion of the rectum 10 extends downward from the sigmoid flexure 14. This portion of the rectum 10 is almost completely surrounded by the peritoneum. A mucous membrane lines this portion of the rectum 10. The mucous membrane is thicker, of a darker color, and more vascular than elsewhere in the colon.

The superior portion of the rectum 10 contains a number of permanent folds of a semi-lunar shape, which are called the Houston valves 18. As FIG. 1 shows, there are usually three Houston valves 18. Sometimes a fourth is present, and occasionally only two are found.

When the rectum 10 is empty, the Houston valves 18 overlap each other. The valves 18 support the weight of fecal matter, to slow its descent toward the anal orifice 16. When the inferior or lower part of the rectum 10 is contracted to expel fecal matter, a number of additional folds develop in the mucous membrane of the superior portion of the rectum 10, to urge fecal matter downward.

The middle portion of the rectum 10 is covered anteriorly and laterally by peritoneum as it extends from the superior portion. However, as the rectum 10 extends further downward, the lateral peritoneum gradually recedes.

The lower or inferior portion of the rectum 10 is called the anal canal 20. It typically extends about 4 to 5 cm above the anal orifice 16. The anal canal 20 is invested by the internal sphincter muscle 22, supported by the Levatores ani muscle 24, and surrounded at its termination by the external sphincter muscle 26. The fat of the ischio-rectal fossae 28 laterally surrounds the anal canal 20.

The external sphincter muscle 26 is a thin flat plane of muscular fibers, measuring about 5 cm in length. It is always in a state of tonic contraction to keep the anal orifice 16 closed. In an empty condition, the anal canal 20 therefore has the appearance of a longitudinal slit. The external sphincter muscle 26 can voluntarily be placed in a greater condition of contraction, to more firmly occlude the anal orifice 16.

The internal sphincter muscle 22 is a muscular ring that surrounds the lower extremity of the rectum 10 for about 2 cm. Its inferior border is contiguous with the external sphincter muscle 26. However, the functions of the two sphincter muscles 22 and 26 are separate. Unlike the external sphincter muscle 26, the internal sphincter muscle 22 is an involuntary muscle. Together, the voluntary external sphincter muscle 26 works with the involuntary internal sphincter muscle 22 to occlude the anal orifice 16. The internal sphincter muscle 22 contributes about 85% of the resting tone of the anal canal 20, to keep fecal material in the rectum 10 until time of controlled expulsion.

The levator ani muscle 24 is a broad, thin muscle situated on each side of the pelvis. This muscle supports the lower end of the rectum 10 and bladder during the controlled efforts of expulsion. A pectinate (dentate) line 30 is defined about 2.5 to 3 cm above the anal orifice 16. The superior extent of the external sphincter muscle 26 extends about 5 cm above the pectinate (dentate) line 30. The superior extent of the internal sphincter muscle 22 extends about 2 to 2.5 cm above the pectinate (dentate) line.

Sensitive mucosal tissue, called the anoderm, lines the anal canal 20 below the pectinate line 30. Anoderm tissue is sensitive to contact with fecal material. When contacting anoderm tissue, the sensed presence of fecal material excites a sensation demanding discharge.

Mucosal tissue immediately above the pectinate line 30, called the anal columns, is also sensitive to the presence of fecal material. The anal columns provide sensory information that discriminates among different types and textures of fecal material, thereby aiding in overall control of the discharge of fecal material.

Because of their important sensory functions, treatment of the rectum 10 should guard against damage to the mucosal tissue below and above the pectinate (dentate) line 30. This sensitive mucosal tissue may be damaged, e.g., by exposure to abnormal heat, and typically do not regenerate after thermal injury.

In a person suffering from fecal incontinence, the external sphincter muscle 26, or the internal sphincter muscle 22, or both lose their tone. As a result, the anal orifice 16 is not occluded. Fecal material descends without control, to spontaneously excite the sensitive anoderm tissue to demand immediate discharge.

It should be noted that the views of the rectum 10 and anal canal 20 shown in FIG. 1, and elsewhere in the drawings, are not intended to be strictly accurate in an anatomic sense. The drawings show the rectum 10 and anal canal 20 in somewhat diagrammatic form to demonstrate the features of the invention.

II. System for Treating Fecal Incontinence

Figure 2:
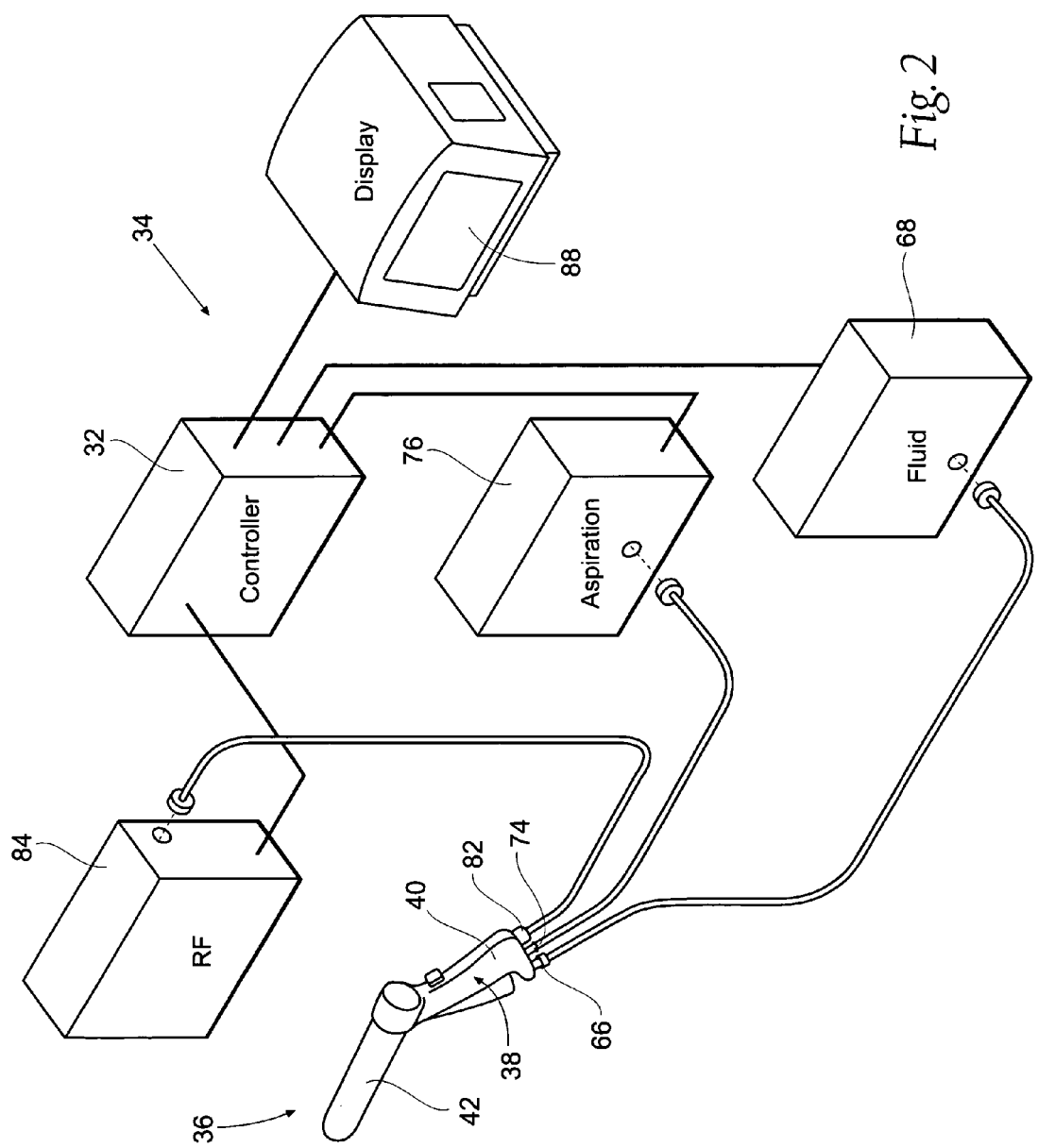
FIG. 2 is a diagrammatic view of a system for treating sphincters and adjoining tissue regions in the rectum and anal canal.

FIG. 2 shows a system 34 for treating dysfunction of the external sphincter muscle 26, or internal sphincter muscle 22, or both.

The system 34 includes a treatment device 36. The device 36 can be constructed in various ways. In the embodiment illustrated in FIGS. 3 and 4, the device 36 includes a hand piece 38 made, e.g., from molded plastic. The hand piece 38 includes a handle grip 40, which is sized to be conveniently held by a physician, in the same fashion as, e.g., an anuscope.

The handle grip 40 carries a hollow, tubular barrel 42, which projects outward from the grip 40. The barrel 42 terminates with a blunt, rounded distal end 44. The barrel 42 has an outside diameter that is sized and configured for insertion into the rectum 10 through the anal orifice 16 (see FIG. 7). The rounded distal end 44 is configured to aid passage of the barrel 42 through the anal canal, without need for a separate introducer.

The wall of the barrel 42 is preferably made from a transparent, molded plastic material. In this arrangement, the handle grip 40 includes a viewing port 46 that allows a physician to look into the hollow interior of the barrel 42. A light pipe 152, stabilized by a bracket 154 within the barrel 42 (see FIGS. 5A and 5B), can be coupled to a source of light to illuminate the distal end of the barrel 42. The physician may also wear a head band with a light source. Looking through the viewing port 46 (see, e.g., FIG. 7), the physician can visualize surrounding tissue through the transparent wall of the barrel 42 to locate the barrel 42 at a desired depth of insertion into the rectum 10, as will be described in greater detail later. Alternatively, the physician may look through the side of the barrel 42 at its proximal end to view tissue through the transparent wall of the barrel 42 at a more distal location.

Figure 4:
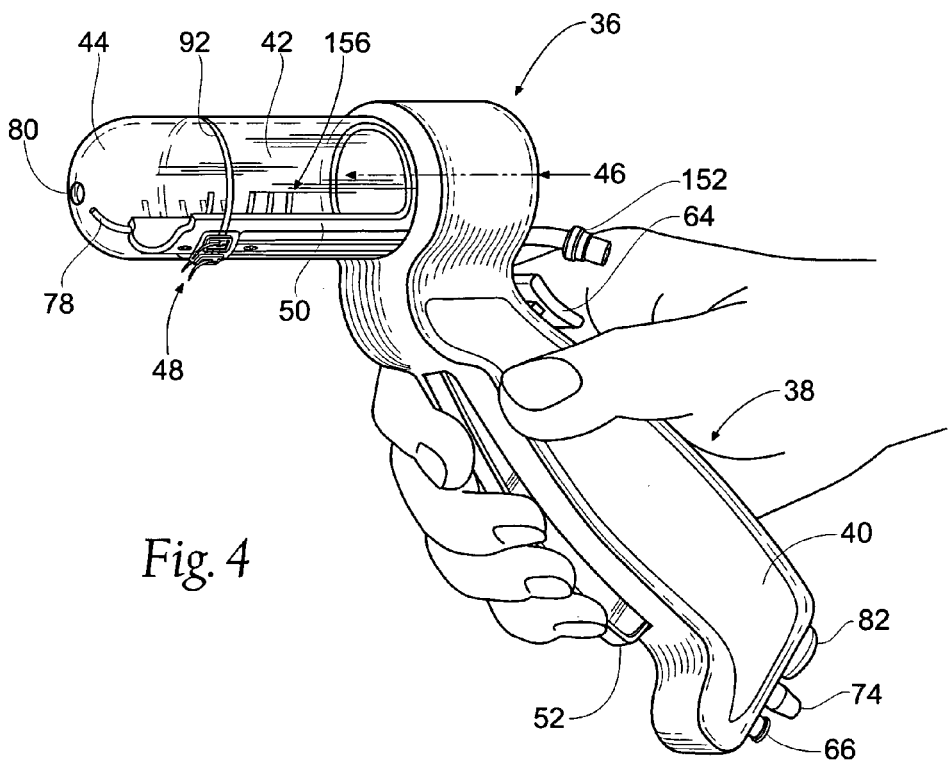
FIG. 4 is a perspective view of the treatment device shown in FIG. 3, with the energy application electrodes extended for use after deployment of the treatment device.

As FIG. 4 shows, the barrel 42 carries an array of needle electrodes 48 that can be selectively deployed into tissue surrounding the barrel 42. The electrodes 48 have sufficient distal sharpness and strength, when deployed, to penetrate a desired depth into the internal and/or external sphincter muscle 22 and/or 26 (see FIG. 8). For this purpose, the distal ends of the needle electrodes 48 are desirably normally biased with an antegrade bend. The desired depth of penetration can range from about 7 mm to about 8 mm from the inside wall of the rectum 10.

As will be described in greater detail later, ablation energy can be applied through the electrodes 48 to create one or more lesions, or a prescribed pattern of lesions, below the mucosal surface 76 of the rectum 10. Natural healing of the subsurface lesions in the rectum 10 can lead to a physical tightening and/or reduced compliance of the external or internal sphincter muscle 22 or 26, or both muscles 22 and 26. The physical tightening of one or both of these muscles 22 or 26 can restore normal closure function, thereby providing therapy for fecal incontinence.

Figure 6A:
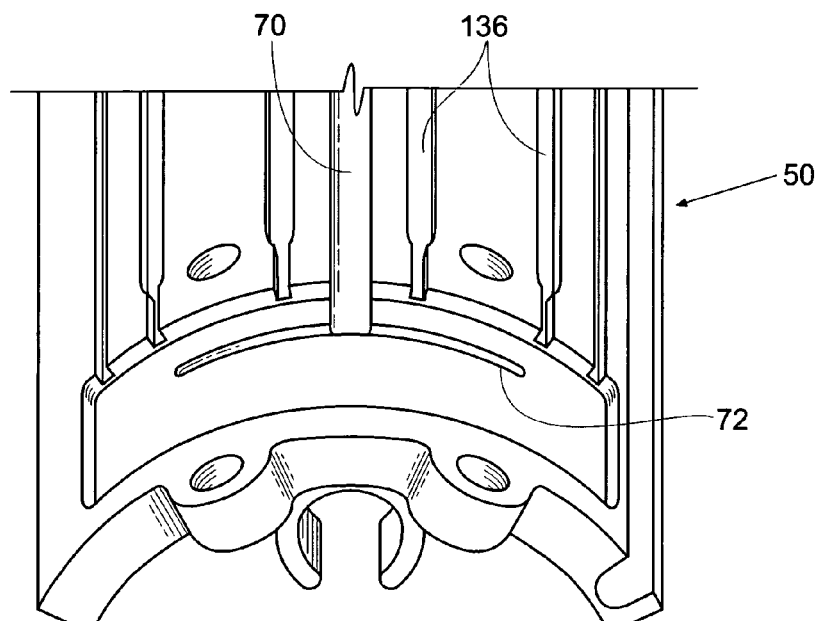
FIG. 6A is an enlarged view of the carrier which guides the electrodes and forms an irrigation manifold that conveys irrigation fluid to the site of each electrode.

The array of electrodes 48 can be configured and mounted for deployment from the barrel 42 is various ways. In one representative embodiment (see FIGS. 3 and 4), the barrel 42 includes an electrode carrier 50. The carrier 50 can comprise, e.g., a molded plastic part with a preformed pattern of recesses that define slots or channels 136, as FIG. 6A also shows. The carrier 50 can be mounted to the interior of the barrel 42 using, e.g., adhesive, or fasteners, or snap-fit or the heat-staked posts 73, as FIGS. 6D and 6E best show.

Figure 6B:
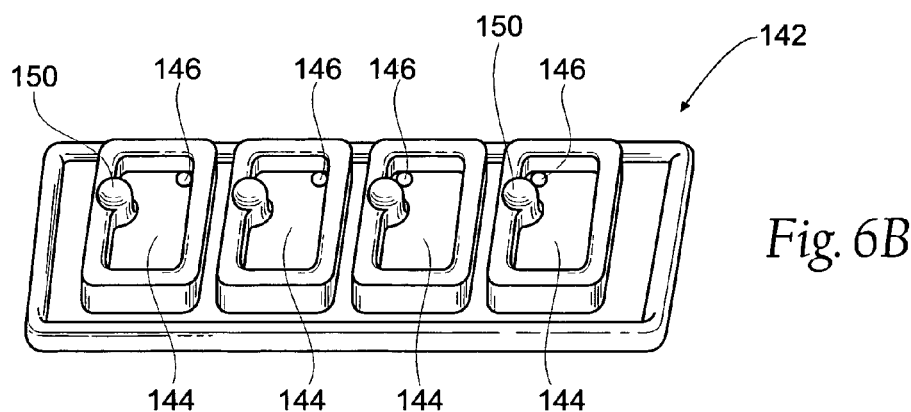
FIGS. 6B and 6C are, respectively, top and bottom view of a silicone seal assembly that is rests over the irrigation manifold shown in FIG. 6A.
Figure 6C:
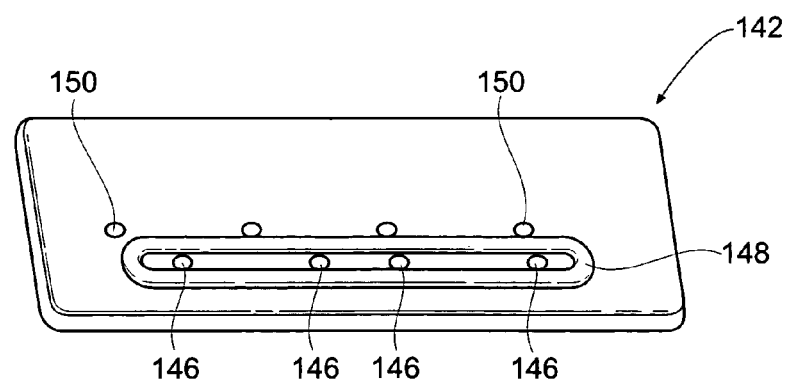
Figure 6D:
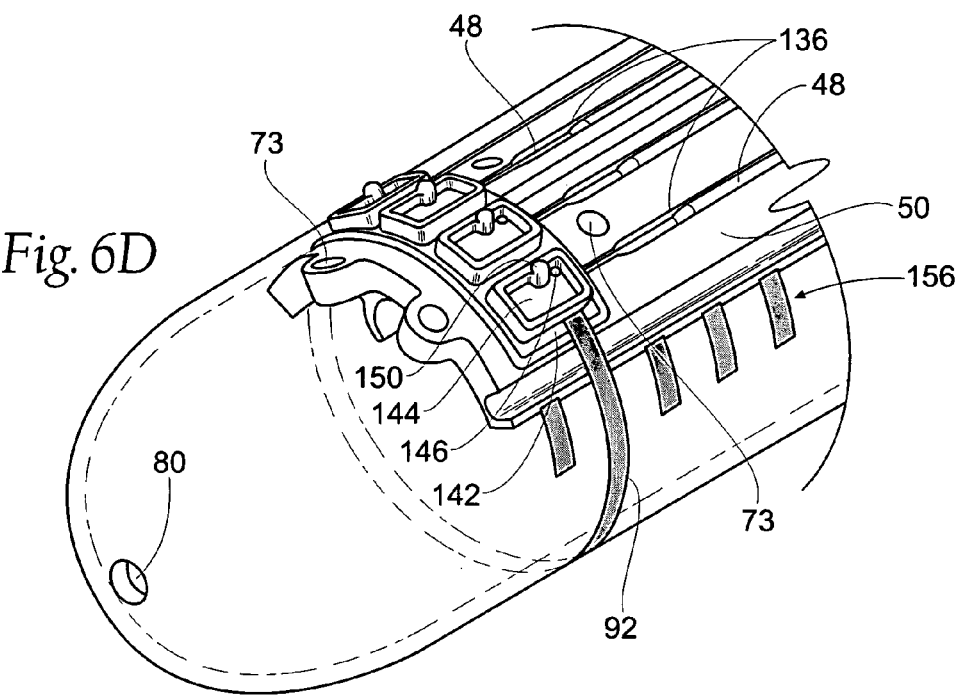
FIG. 6D is an assembled view of the silicone seal shown in FIGS. 6B and 6C secured in place over the irrigation manifold, the electrodes being shown in a retracted position.
Figure 6E:
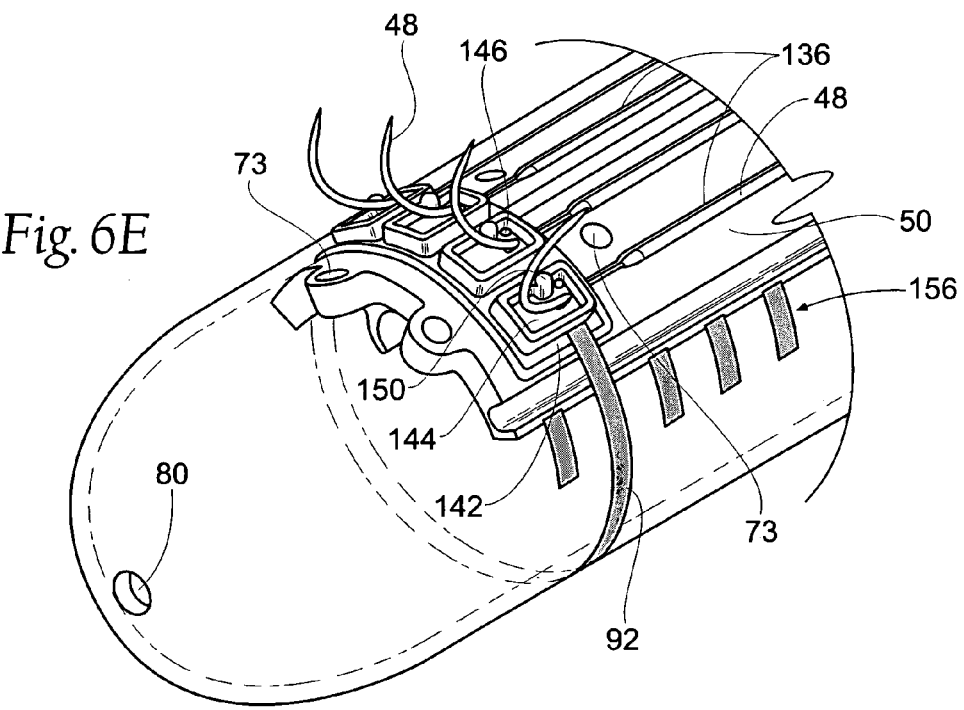
FIG. 6E is an assembled view of the silicone seal shown in FIGS. 6B and 6C secured in place over the irrigation manifold, the electrodes being shown in an extended position, passing through the silicone seal assembly.

The array of needle electrodes 48 are movably contained in certain of the channels 136 in the carrier 50 (see FIGS. 6D and 6E). The needle electrodes 48 are carried in the carrier 50 in a side-by-side relationship along an arcuate segment of the barrel 42. In the illustrated embodiment, the needle electrodes 48 occupy an arc of about 67.5 degrees along the circumference of the barrel 42.

Figure 3:
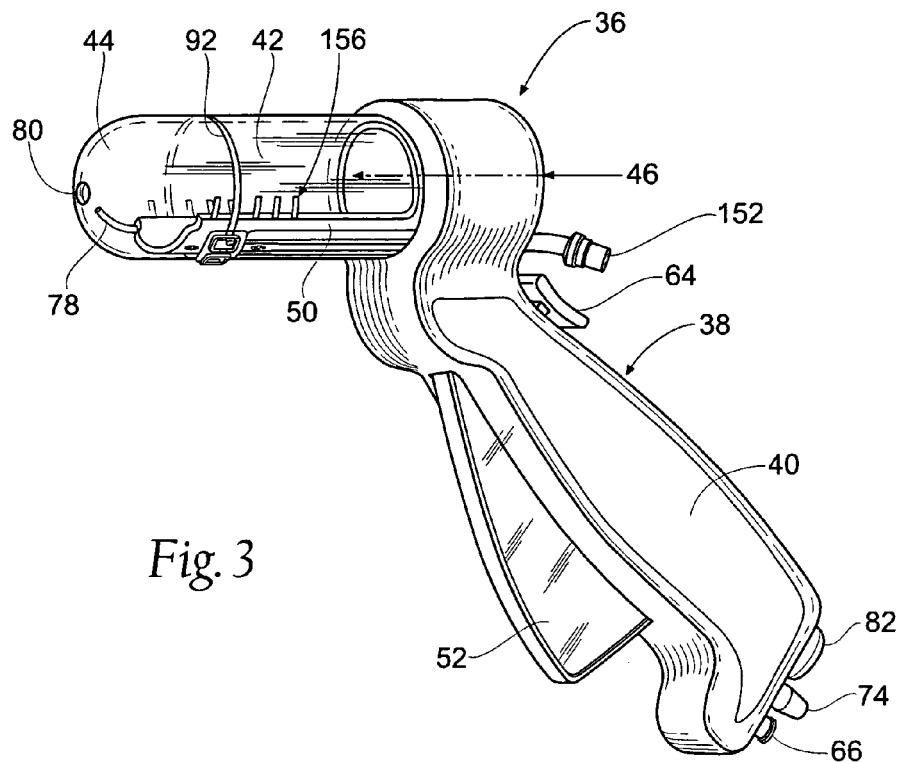
FIG. 3 is a perspective view of a treatment device usable in association with the system shown in FIG. 2, with the energy application electrodes withdrawn for deployment of the treatment device.
Figure 5A:
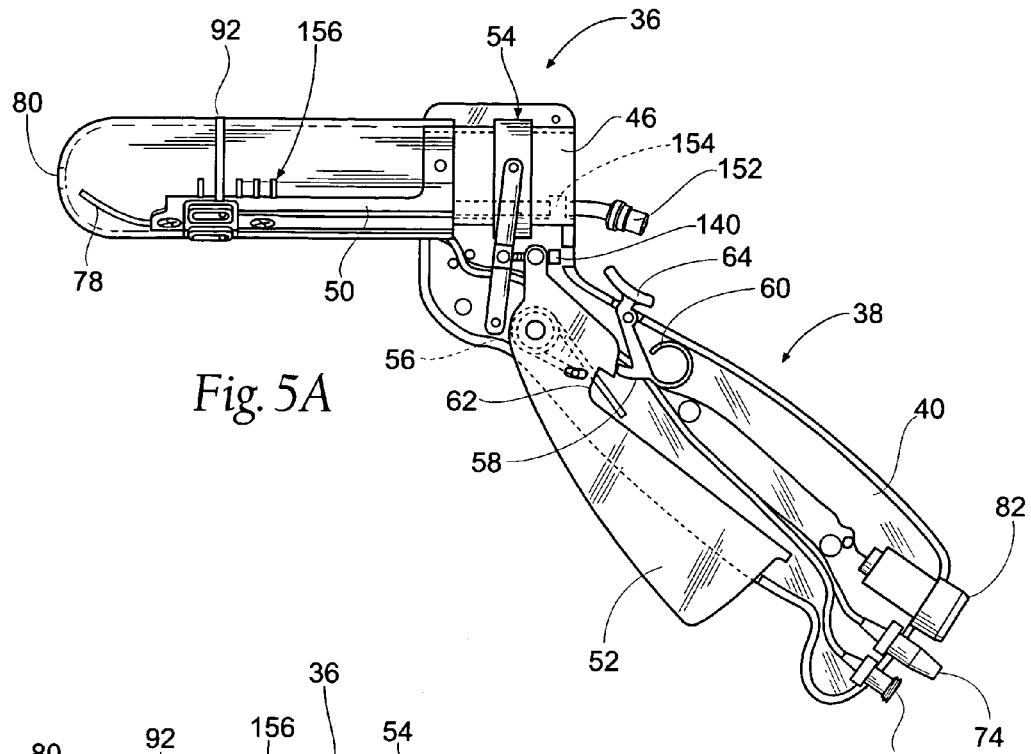
FIG. 5A is a side view of the treatment device shown in FIG. 3, with a portion of the handle grip removed to show the mechanical linkage coupling the pull lever to the electrodes, the electrodes being shown withdrawn.
Figure 5B:
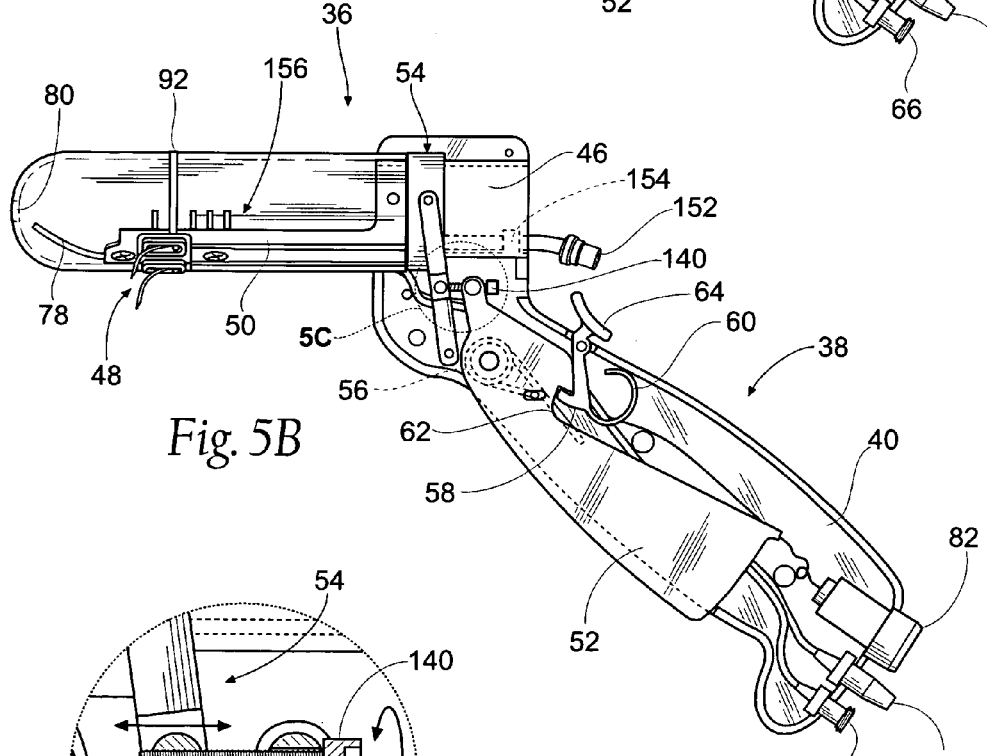
FIG. 5B is a side view of the treatment device shown in FIG. 4, with a portion of the handle grip removed to show the mechanical linkage coupling the pull lever to the electrodes, the electrodes being shown extended.
Figure 5C:
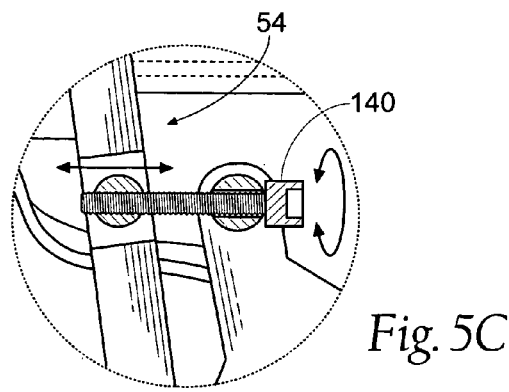
FIG. 5C is an enlarged view of a portion of the linkage shown in FIGS. 5A and 5B, showing the presence of a threaded nut to enable fine adjustment of the extension length of the electrodes during manufacture.

As FIGS. 3 and 4 show, a finger-operated pull lever 52 on the handle grip serves to slide the needle electrodes 48 within the channels. As FIGS. 5A and 5B show, an intermediate mechanical linkage 54 couples the electrodes 48 as a group to the pull lever 52. As FIG. 6C shows, the mechanical linkage 54 can include an adjustment mechanism 140, comprising e.g., a screw, nut, and busing assembly, for adjusting the length of electrode extension during manufacturing. By depressing the pull lever 52 like a trigger (as FIG. 5B shows), the distal ends of the needle electrodes 48 are moved as a unit between a retracted position within the barrel 42 (FIGS. 3 and 5A) and an extended, position projecting through slots outside the barrel 42 (as shown in FIGS. 4 and 5B), for penetrating tissue. A torsion spring 56 (see FIGS. 5A and 5B) normally biases the pull lever 52 to maintain the needle electrodes 48 in their retracted position. Other spring or biasing mechanisms can be provided for the same purpose.

A locking pawl 58 in the handle grip 40 is biased by a spring 60 to swing into a detent 62 in the pull lever 52 as the pull lever 52 is depressed (as FIGS. 5A and 5B show). Within the detent 62, the pawl 58 resists movement of the pull lever 52 out of the depressed position, thereby locking the needle electrodes 48 in their extended position. The locking pawl 58 includes a release button 64, which projects outside the back of handle grip 40 (i.e., on the side opposite to the pull lever 52). Thumb pressure on the button 64 overcomes the biasing force of the spring 60 and frees the pawl 58 from the detent 62. The counter force of the spring 56 serves to urge the pull lever 52 toward the neutral position, thereby moving the needle electrodes 48 back to their normally retracted positions.

Further details of a mechanical linkage 54 that can be used to withdraw and extend the electrodes 48 can be found in U.S. Pat. No. 6,645,201, which is incorporated herein by reference.

A fitting 66 on the handle grip 40 is intended to be coupled to an external fluid delivery apparatus 68 (see FIG. 2). The apparatus 68 conveys a cooling liquid into contact with mucosal tissue regions adjacent the electrodes 48. The cooling fluid preserves and protects the exterior muscosal tissue against damage while submucosal lesions are formed.

In the illustrated embodiment (see FIG. 6A), tubing 70 contained within a channel in the carrier 50 routes the cooling fluid to a fluid trough or manifold 72 formed in the carrier 50 distal to but near the termination of the channels 136 through which the electrodes 48 slide. A seal assembly 142 (see FIGS. 6B and 6C) is fitted, e.g., by adhesive or mechanical compression, over the fluid manifold 72, as FIGS. 6D and 6E best show). The seal assembly 142 can be made of various non-porous materials, e.g., silicone or thermoplastic elastomers.

In the illustrated embodiment, the silicone seal assembly 142 includes an array of pre-formed bays 144, equal in number to the number of electrodes 48. Each bay 144 includes a port 146, which communicates with the fluid manifold 72. An o-ring seal 148 (see FIG. 6C) on the back side of the seal assembly 142 desirably encircles the manifold 72, to seal around the ports 146.

Irrigation fluid entering the manifold 72 flows through the ports 146 into the bays 144 and thence into contact with tissue. The electrodes 48, when extended, pierce the silicone material near each port 146 (see FIG. 6E) within each bay 144. The silicone material acts as a septum, sealing about the electrodes 48. In this way, irrigation fluid can be distributed in a reliable fashion near each electrode 48.

In the illustrated embodiment, posts 150 are pre-formed in the silicone seal assembly 142 near each port 146. Thermocouples or other forms of temperature sensing devices 86 are routed to each post 150 to provide the capability of sensing temperature near each electrode 48.

Another fitting 74 on the handle grip 40 is intended to be coupled to an external aspirating apparatus 76 (see FIG. 2). The apparatus 76 aspirates liquid from the tissue region occupied by the barrel 42. In the illustrated embodiment (see FIGS. 3 and 4), tubing 78 contained within a channel in the carrier 50 extends into the distal end 44 of the barrel 42, to communicate with an aspiration port 80 formed in the barrel 42. Liquid external to the barrel 42 is drawn through the port 80 into the tubing 78 by aspiration for discharge. Fittings 66 and 74 are desirably spaced apart a sufficient distance to permit coupling to a syringe, so that positive or negative pressure can be applied to dislodge foreign matter.

A connector 82 on the handle grip 40 is intended to be coupled to an external generator 84 (see FIG. 2). The generator 84 supplies treatment energy to the electrodes 48. In the illustrated embodiment, the generator 84 supplies radio frequency energy, e.g., having a frequency in the range of about 400 kHz to about 10 mHz. To transmit radio frequency energy, the electrodes 48 can be formed from various energy transmitting materials, e.g., nickel titanium, stainless steel, e.g., 304 stainless steel, or, a combination of nickel titanium and stainless steel. An electrical insulating material is desirably coated about the needle electrodes 48, except for a prescribed region of the distal ends, where radio frequency energy is applied to tissue.

Of course, other forms of energy can be applied, e.g., coherent or incoherent light; heated or cooled fluid; resistive heating; microwave; ultrasound; a tissue ablation fluid; or cryogenic fluid. The form and fit of the electrodes 48 will, of course, differ to accommodate application of other forms of energy.

In the illustrated embodiment, wiring channeled through the carrier 50 couples the electrodes 48 to the connector 82. Wiring routed through the carrier 50 can also couple the connector 82 to the thermocouples or temperature sensing devices 86 carried within the posts 150 of the seal assembly 142 or on the electrodes 48 themselves.

The system 34 also includes a controller 32. The controller 32, which preferably includes a central processing unit (CPU), is linked to the generator 84, the fluid delivery apparatus 68, and the aspirating apparatus 76. Alternatively, the aspirating apparatus 76 can comprise a conventional vacuum source typically present in a physician=s suite, which operates continuously, independent of the controller 32.

The controller 32 governs the power levels, cycles, and duration that the radio frequency energy is distributed to the electrodes 48, to achieve and maintain power levels appropriate to achieve the desired treatment objectives. In tandem, the controller 32 also governs the delivery of processing fluid and, if desired, the removal of aspirated material.

The controller 32 includes an input/output (I/O) device 88. The I/O device 88 allows the physician to input control and processing variables, to enable the controller to generate appropriate command signals. The I/O device 88 also receives real time processing feedback information from the temperature sensors 86 associated with the operative element, for processing by the controller 32, e.g., to govern the application of energy and the delivery of processing fluid. The I/O device 88 can also include a graphical user interface (GUI), to graphically present processing information to the physician for viewing or analysis.

III. Use of the System for Treating Fecal Incontinence

In use (see FIG. 7), the physician grasps the handle grip 40 and guides the barrel 42 into the anal canal 20. The pull lever 52 is in the neutral position and not depressed, so the needle electrodes 48 occupy their normal retracted position (as FIG. 7 shows).

"Looking through the viewing port 46 (see FIG. 7), the physician visualizes the pectinate (dentate) line 30 through the barrel 42. Looking through the barrel 42, the physician positions the distal ends of the needle electrodes 48 at a desired location above the pectinate (dentate) line 30. A light source or imaging apparatus can also be inserted into the barrel 42 to provide local illumination, or the physician can wear a headlamp for this purpose."

Figure 7:
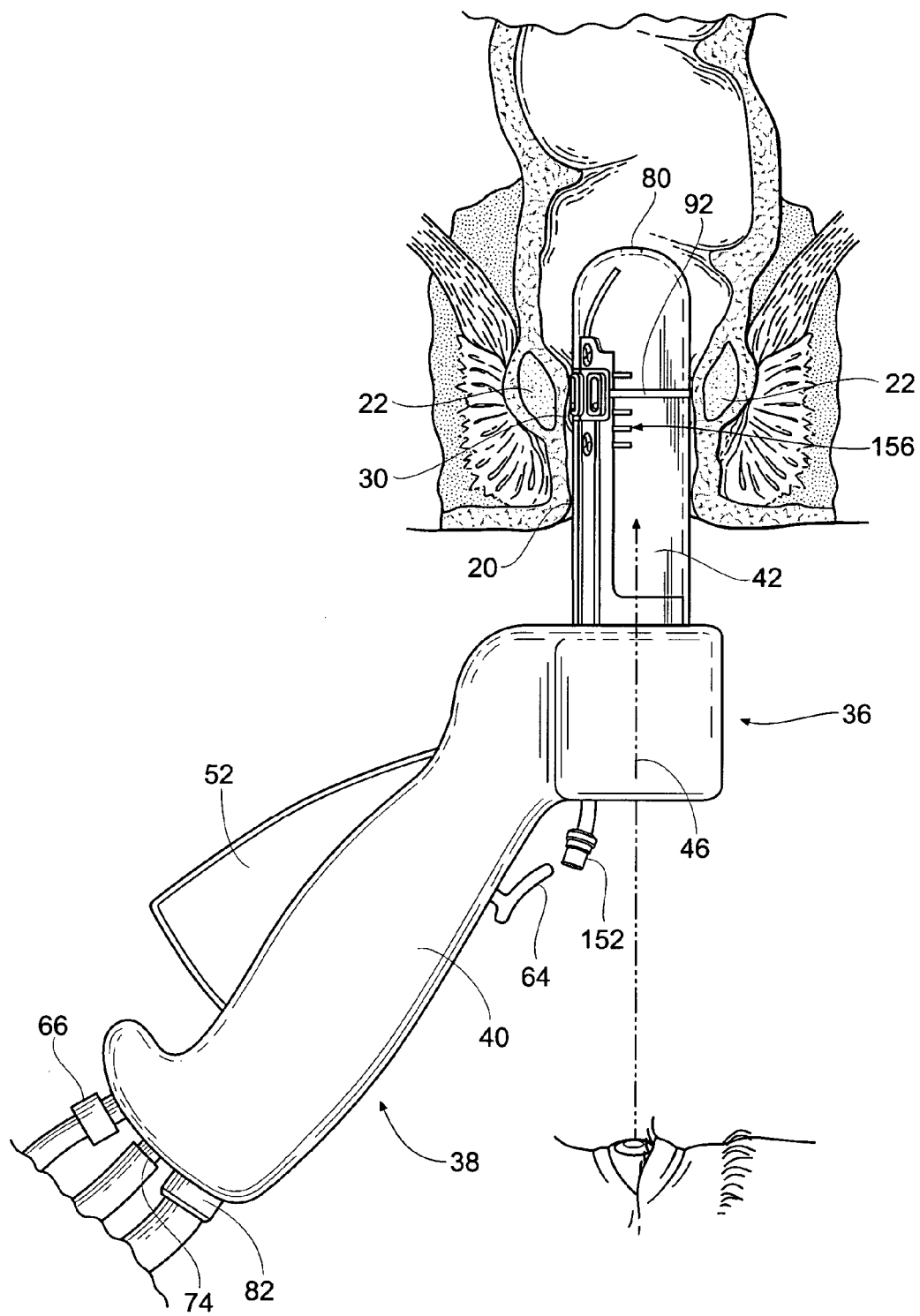
FIG. 7 is an anatomic view of the anal canal, with the treatment device shown in FIGS. 3 and 4 inserted for positioning relative to the dentate line and with the needle electrodes in their retracted position.

As FIG. 7 also shows, the location of the distal ends of needle electrodes 48 can also be marked by an opaque band 92 printed, scribed, or pasted on the outside of the barrel 42. The band 92 visually aids the physician in aligning the electrodes 48 at the desired tissue location with respect to the dentate line 30. Additional arrays of subsidiary marker bands 156 positioned fore and aft of the main band 92—spaced apart by, e.g. 5 to 10 mm axially and spanning a 45° to 90° radial quadrant—may be provided in association with the main band 92, to aid the physician in locating the barrel 42, especially when it is desired to form a composite lesion pattern, as will be described later.

Figure 8:
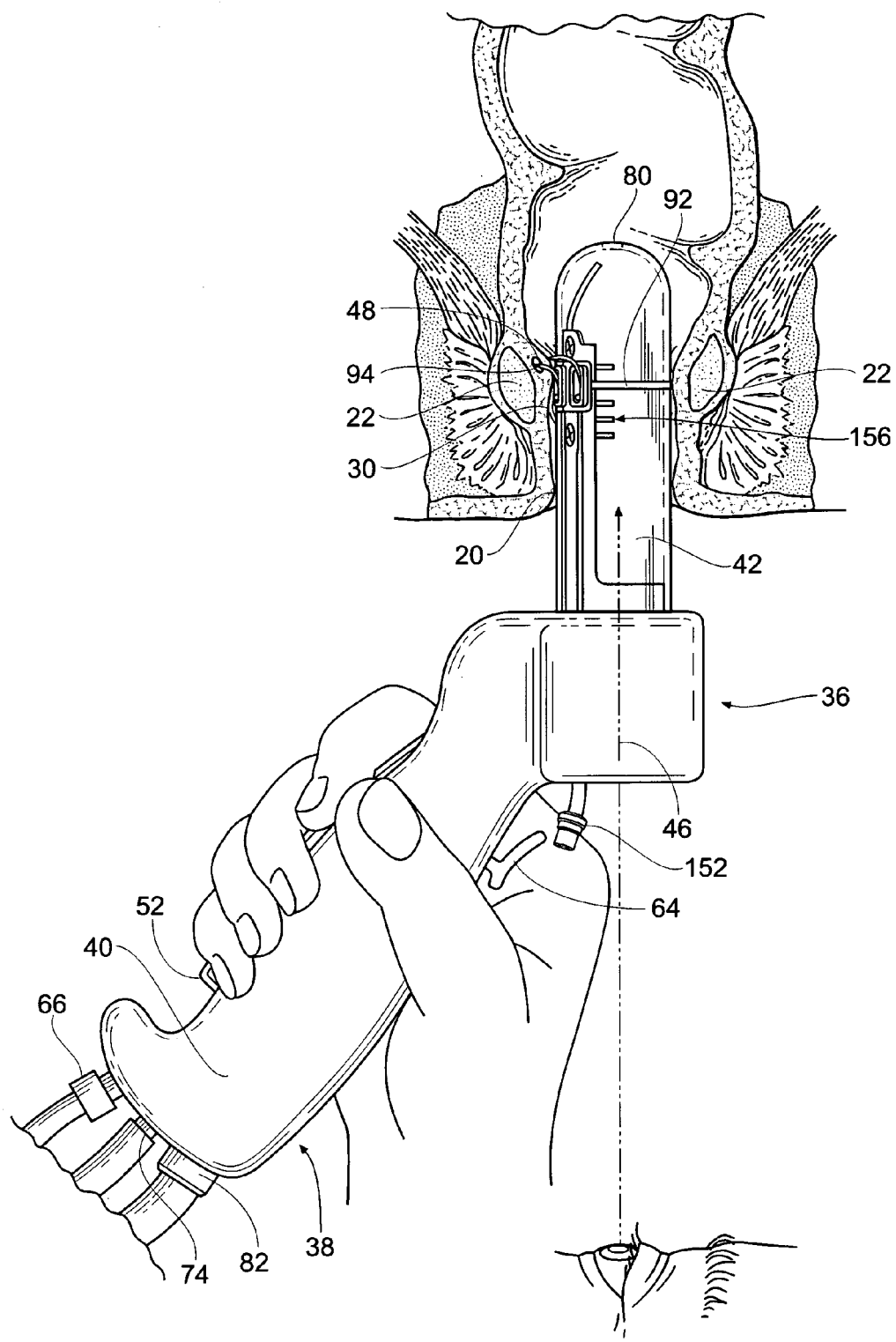
FIG. 8 is an anatomic view of the anal canal, with the treatment device shown in FIG. 7 with the needle electrodes in their extended position inside the internal sphincter muscle.

Once the distal end of the barrel 42 is located at the targeted site, the physician depresses the pull lever 52 (see FIG. 8). The needle electrodes 48 advance to and lock in their extended positions. The trigger lock is designed to provide an anti-tenting feature as well (the needles initially extend longer to poke through tenting tissue, then fall back to a slightly short treatment position). The distal ends of the electrodes 48 pierce and pass through the mucosal tissue into the muscle tissue of the target sphincter muscle. In FIG. 8, the distal end of the electrodes are shown penetrating the involuntary, internal sphincter muscle 22.

The physician commands the controller 32 to apply radio frequency energy through the needle electrodes 48. The energy can be applied simultaneously by all electrodes 48, or in any desired sequence.

The energy ohmically heats the muscle tissue. The controller 32 samples temperatures sensed by the sensors 86 to control the application of energy, to achieve tissue temperatures in the targeted muscle tissue in the range of 551 C to 951 C.

The fluid delivery apparatus 68 conveys cooling fluid for discharge at the treatment site, to cool the mucosal surface while energy is being applied by the needle electrodes 48. The aspirating apparatus 76 draws aspirated material and the processing fluid through the tubing 78 for discharge. The array of needle electrodes 48 creates a first pattern 94 of multiple lesions (see FIG. 11).

Upon the satisfactory creation of the first lesion pattern 94, as just described, the physician actuates the button 64 to release the locking pawl 58 from the detent 62. The pull lever 52 returns to the spring-biased neutral position, thereby moving the needle electrodes 48 back to their retracted positions.

Figure 9:
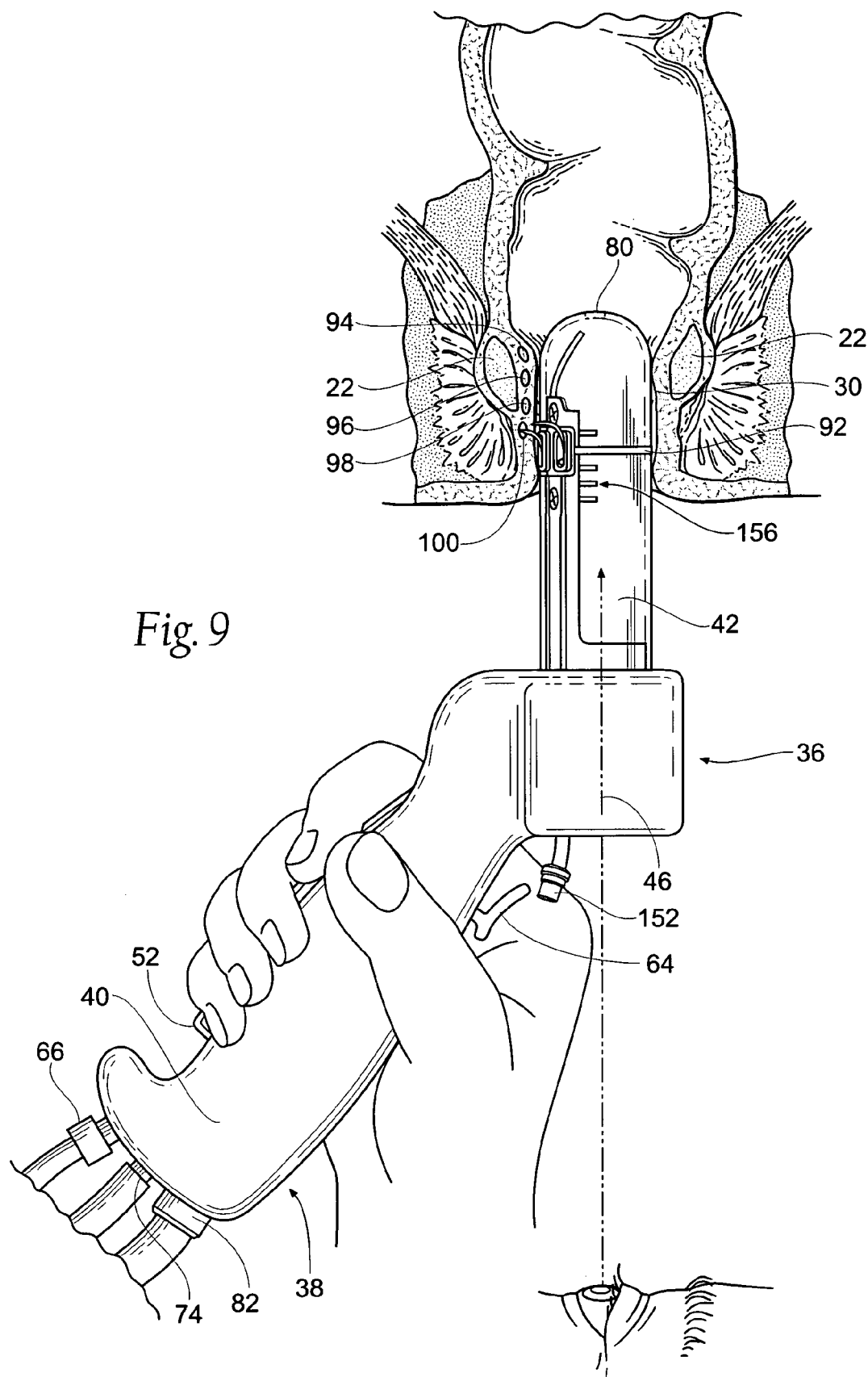
FIG. 9 is an anatomic view of the anal canal, with the treatment device shown in FIG. 8, having been moved sequentially downward along the canal to form a first series of axially spaced lesion quadrants.

Still grasping the hand grip 40 and visualizing through the viewing port 46, the physician moves the barrel 42 axially downward to another location spaced from the first lesion pattern 94. The subsidiary marker bands 156 aid in positioning the barrel 42. The physician again deploys the needle electrodes 48 and performs another lesion generating sequence (see FIG. 10). The physician repeats this sequence of steps until additional number of lesion patterns are formed within axially spaced quadrants (FIG. 9 shows three additional patterns 96, 98, 100)(also see FIG. 11).

Figure 10:
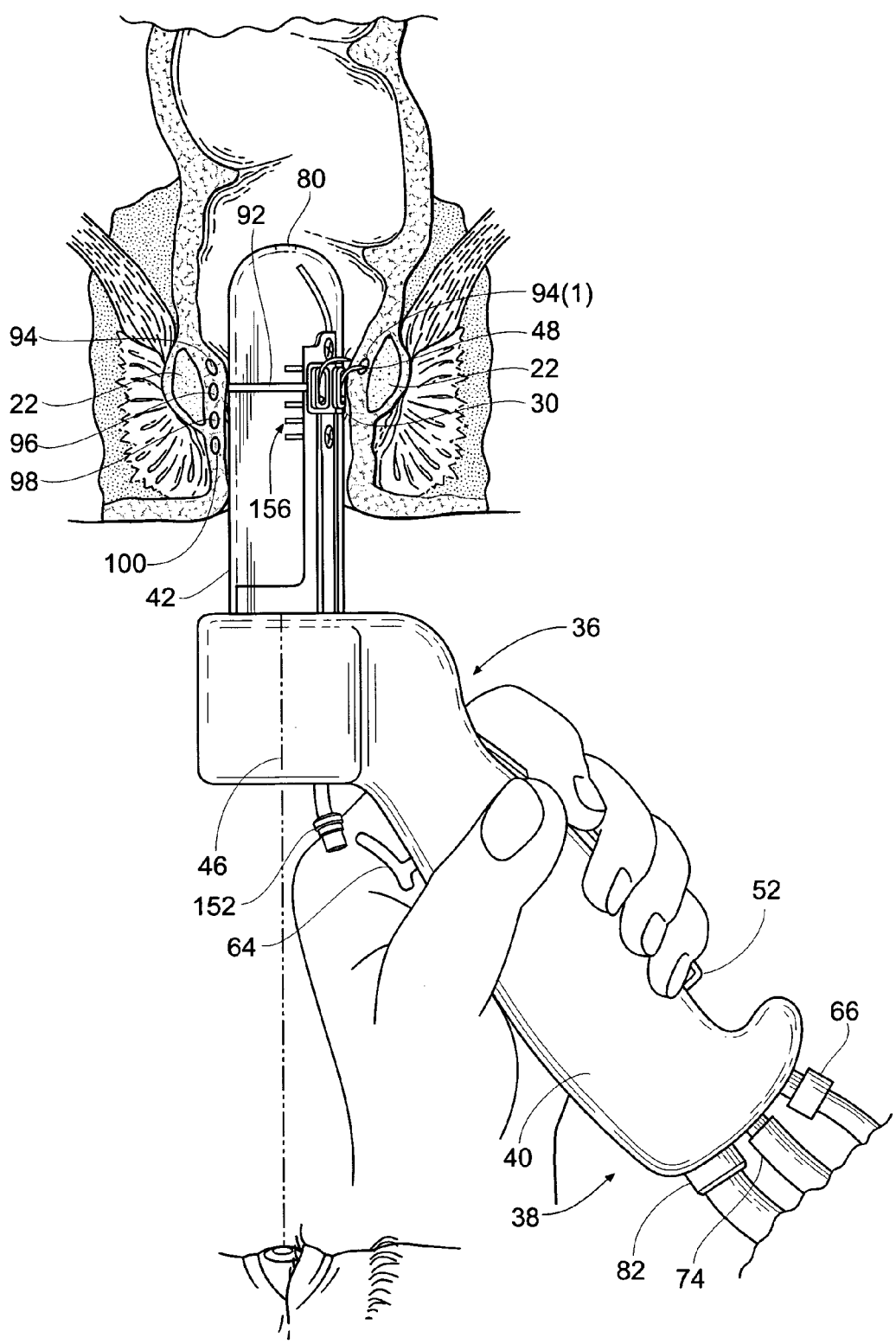
FIG. 10 is an anatomic view of the anal canal shown in FIG. 9, with the treatment device shown in FIG. 9 rotated to a new position and the needle electrodes in their extended positions to form another series of axially spaced lesion quadrants rotationally spaced from the first series.

Still grasping the hand grip 40 and visualizing through the viewing port 46, the physician rotates the barrel 42 a selected arcuate distance at the level of the first lesion pattern 94 (see FIG. 10). For example, the physician can rotate the barrel 42 by forty-five degrees or by ninety degrees.

The physician again deploys the needle electrodes 48 and performs another lesion generating sequence at the level of lesion pattern 94 (see FIG. 10). The physician then moves the barrel axially downward at a number of axially spaced levels generally aligned with lesion patterns 96, 98, and 100. Second lesion pattern quadrants 94(2), 96(2), 98(2), and 98(2) (see FIG. 11) are created, circumferentially spaced from the first lesion pattern quadrants 94, 96, 98, and 100.

Figure 11:
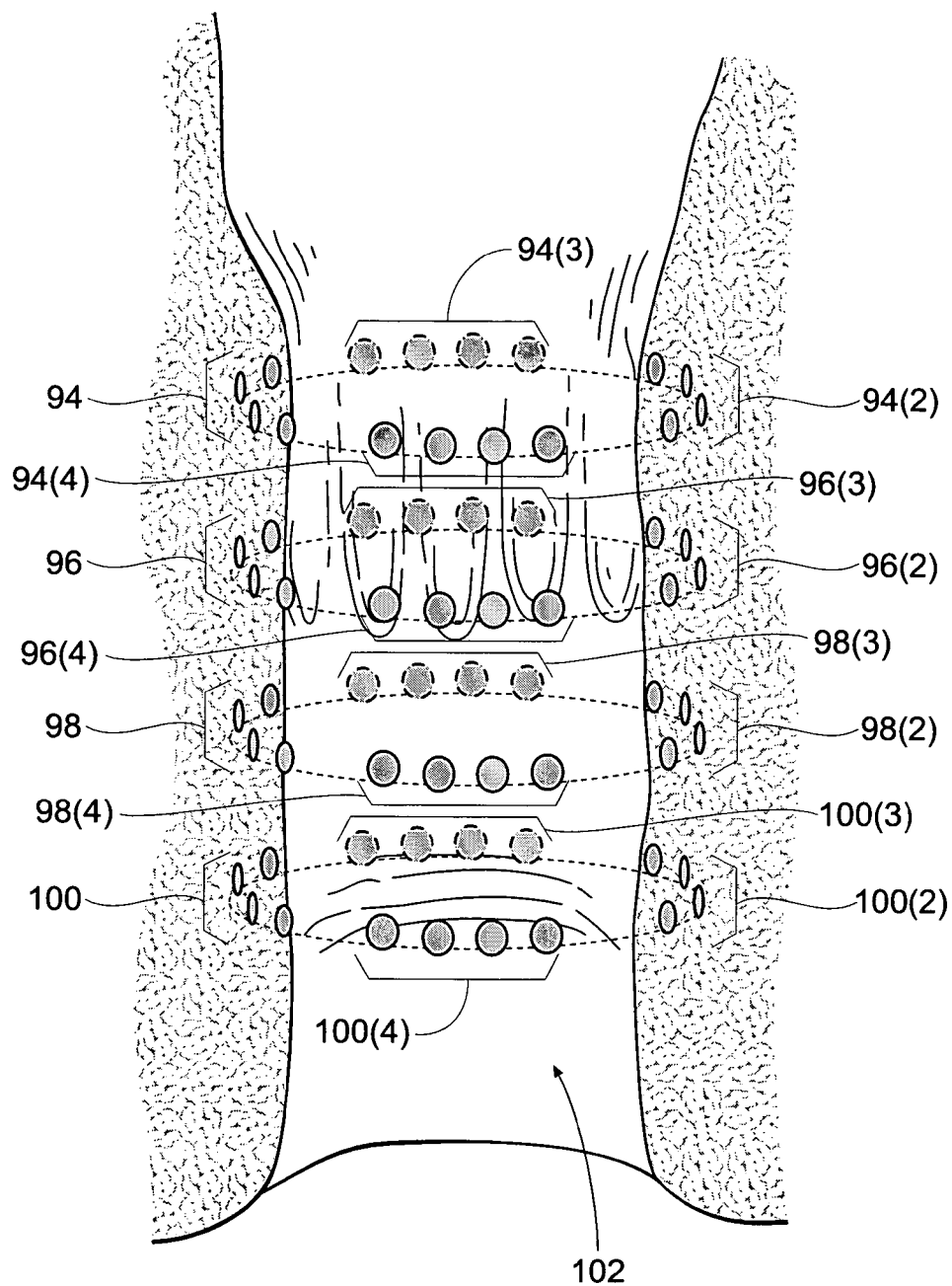
FIG. 11 is an anatomic view of a complex lesion pattern formed in the internal sphincter muscle by manipulating the device shown in FIGS. 3 and 4 in the manner shown in FIGS. 7 to 10.

The physician can repeat the above described sequence two additional times, rotating the barrel 42 at successive intervals and axially repositioning the barrel 42 to form third and fourth lesion pattern quadrants 94(3)-100(3) and 94(4)-100(4) (see FIG. 11). This protocol forms a composite lesion pattern 102 (see FIG. 11), which provides a density of lesions in the targeted sphincter tissue region to provoke a desired contraction of the sphincter tissue.

Of course, the physician may decide to create the composite lesion pattern 102 in a different sequence. For example, the physician may decide to form a given level of lesion pattern quadrants—e.g., 94, 94(1), 94(3), and 94(4)—by maintaining the barrel 42 at the chosen level and rotating the barrel 42 at successive intervals, and then axially move downward to the next level and rotating the barrel 42 to form the next level of lesion pattern quadrants 96, 96(2), 96(3), and 98(3), and so on until the composite lesion pattern 102 us formed. It should be appreciated that the ultimate objective—to provide a density of lesions in the targeted sphincter tissue region to provoke a desired contraction of the sphincter tissue—can be achieved in various alternative ways using the device 10.

IV. Accommodating Different Anatomic Forms and Structures

The system 34 desirably has the capability to accommodate the treatment of a population of different individuals, who present different anatomic forms and structures in the region of the rectum and/or anal orifice. Various illustrative embodiments are shown, which provide treatment devices that can adapt to the anatomic form and structure of different individuals in these region.

A. Different Barrel Dimensions

Figure 12:
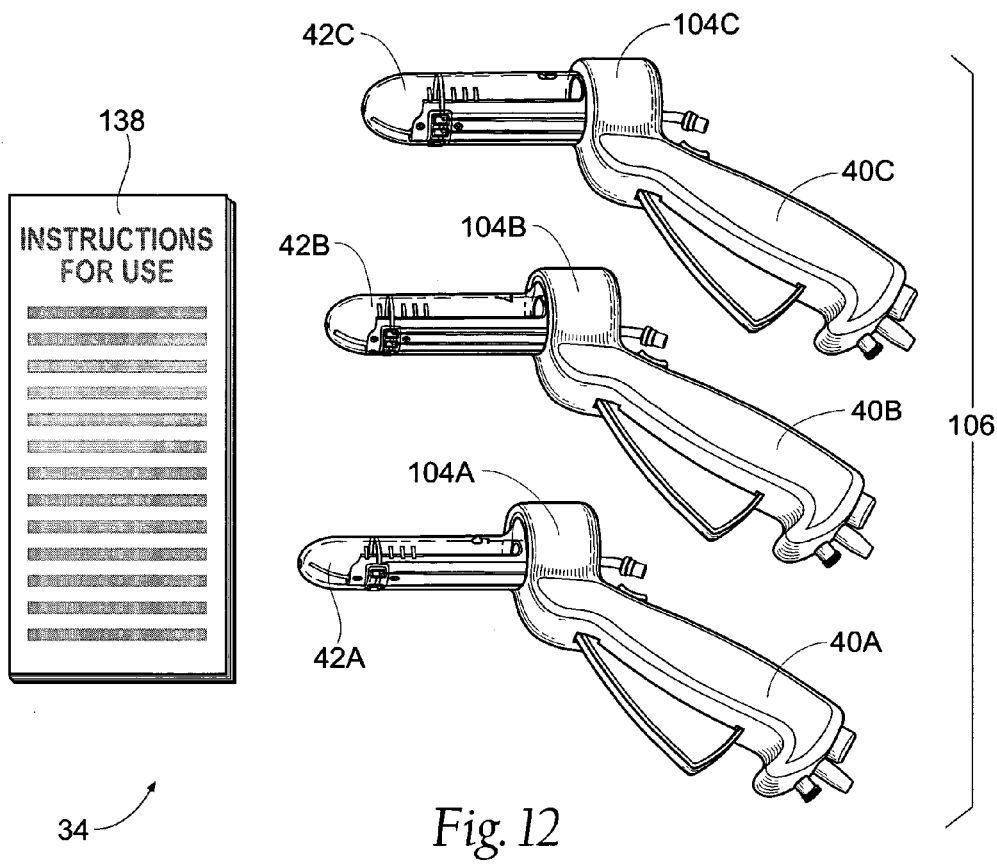
FIG. 12 shows a representative embodiment of a family of treatment devices for treating sphincters and adjoining tissue regions in the rectum and anal canal, the family comprising an assortment of barrels of different dimensions that are configured to adapt to the anatomic form and structure of different individuals in these tissue regions, the family also including instructions for use.

As FIG. 12 shows, in one arrangement, the system 34 can include a family 106 of treatment devices 104A, 104B, and 104C. Each treatment device 104A, 104B, and 104C comprises a handle grip—respectively 40A, 40B, 40C—and a barrel—respectively 42A, 42B, and 42C—of the troupe previously described. Within the family 106, each barrel 42A, 42B, and 42C has a different dimension comprising an outside diameter and/or length, from smallest (barrel 42A), intermediate outside (barrel 42B), to largest (barrel 42C). A representative range of barrel dimensions is 20 mm (smallest), 30 mm (intermediate), and 40 mm (largest). The barrels 42A, 42B, and 42C may have either a round or oval cross section and be marked with indicia indicating its diameter or relative size.

Within the family 106, the handle grip 40A/40B/40C and respective barrel 42A/42B/42C can be provided to form an assembled treatment device 104A, 104B, and 104C (as FIG. 12 shows), intended for single use and subsequent disposal.

Figure 13:
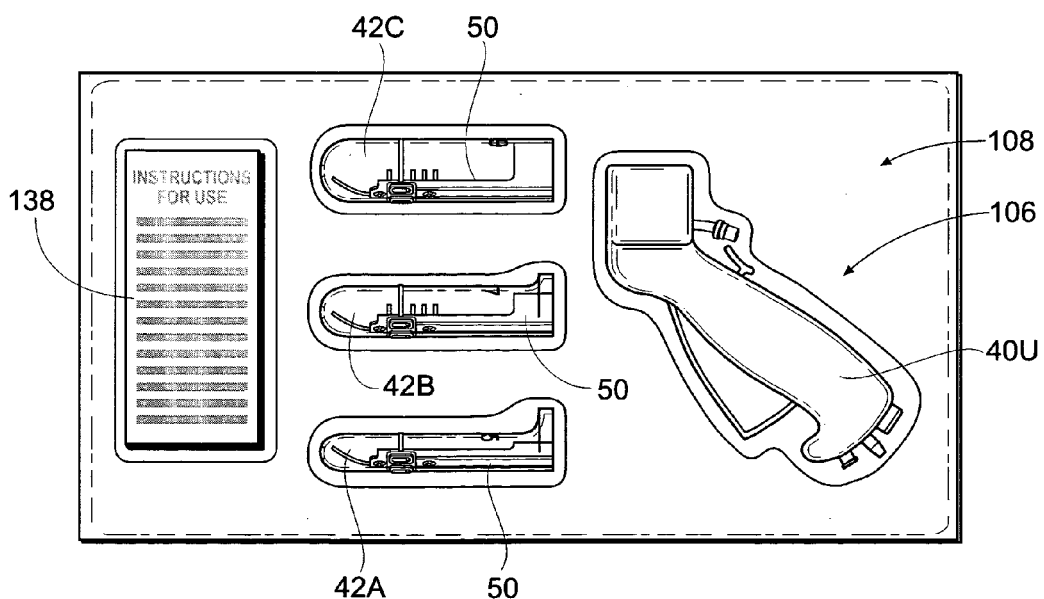
FIG. 13 shows a kit containing another representative embodiment of a family of treatment devices for treating sphincters and adjoining tissue regions in the rectum and anal canal, the family comprising a universal handle that couples to an assortment of barrels of different dimensions that are configured to adapt to the anatomic form and structure of different individuals in these tissue regions, the kit also containing instructions for use.

Alternatively (as FIG. 13 shows), the family 106 can comprise a universal handle grip 40U as a separate component intended for single use or for multiple uses. In this arrangement, the family 106 comprises an assortment of interchangeable barrels 42A, 42B, and 42C of different dimensions. Each barrel 40A, 40B, and 40C comprises a separate, disposable component, including the electrodes 48 and other associated components routed by a carrier 50 within a respective barrel. In this arrangement, the physician can releasably connect a selected barrel 42A, 42B, or 42C to the universal handle grip 40U at time of use, to form the respective treatment device 104A, 104B, or 104C. After use, the selected barrel can be disconnected from the universal handle grip 40U and discarded. Alternatively, the entire formed treatment device 104A, 104B, or 104C can be discarded after use.

The system 34 can provide the family 106 of treatment devices 104A, 104B, and 104C as integrated devices (as FIG. 12 shows), individually prepackaged as single use items in a sterile fashion within peripherally sealed sheets of plastic film material that are torn or peeled away at the instance of use. Alternatively, as FIG. 13 shows, the system 34 can provide the family 106 as a kit 108, with a universal handle grip 40U accompanied by a selection of separate barrels 42A, 42B, and 42C of different dimensions. The kit 106 packages the handle grip 40C and barrels 42A, 42B, and 42C as single use items in a sterile fashion within peripherally sealed sheets of plastic film material that are torn or peeled away at the instance of use.

The system 34 can include, together with the particular treatment device or kit or separately supplied, instructions 138 for using the treatment device 104A, 104, 104C. The instructions for use can include the step of assessing the anatomic requirements of the individual to be treated, and selecting a barrel 42A, 42B, and 42C from among the array of barrels to provide a treatment device based upon the assessed anatomic requirement.

B. Composite Barrel Assembly

Alternatively, as shown in FIGS. 14 and 15, a treatment device 120 can include a handle grip 40 with a composite barrel assembly 110. The composite barrel assembly 110 includes a frame component 112 and a canopy component 114.

The frame component 112 is permanently coupled to the handle grip 40. The frame component 112 supports the carrier 50 and its components, which are secured within the frame component 112 in the same manner already described.

The canopy component 114 is not permanently coupled to the handle grip 40. Instead, the canopy component 114 couples to the frame component 112 in a manner that allows the canopy component 114 to be inserted onto and released from the frame component 112. For example, the canopy component 114 can rest on a slide-on track 116 for insertion and removal from the frame component 112. Alternatively, the canopy component 114 can include a snap-on/snap-off insertion/release that mates with a counterpart release mechanism on the frame component 112.

In this arrangement, the outside diameter of the composite barrel assembly 110 is determined by the dimensions of the frame component 112, which are fixed, as well as the dimensions of the canopy component 114, which can vary among an assortment of canopy components 114. More particularly, the system 34 can include a family of 118 of canopy components 114A, 114B, 114C each having a different dimension, from smallest (canopy component 114A), intermediate (canopy component 114B), to largest (canopy component 114C). The dimensions of the particular canopy component 114A, 114B, or 114C selected for coupling to the frame component 112 dictates the overall final dimension of the composite barrel assembly 110, from smallest, intermediate, to largest. The assembled frame/canopy unit may have either a round or oval cross section. Generally, as smaller canopies are attached to a frame component having the same size, the assembled unit will have an increasingly oval cross section.

The system 34 can provide the treatment device 120 as a prepackaged handle grip 40 with preconnected frame component 112, and a family 118 of separately prepackaged canopy components 114A, 114B, and 114C of different dimensions, as FIG. 14 shows. Alternatively (as FIG. 16 shows), the system 34 can provide the treatment device 120 in a kit 108, comprising a handle grip 40 with a preconnected frame component 112, together with a family 118 of separate canopy components 114A, 114B, 114C of different dimensions. In either form, the treatment device 120 is intended to be a single use item which is discarded after use.

The system 34 can include, together with the particular treatment device 120, or as separately supplied, instructions 138 for using the treatment device 120. The instructions for use can include the step of assessing the anatomic requirements of the individual to be treated, and selecting a canopy component 114A, 114B, and 114C from among the family 118 of canopy components based upon the assessed anatomic requirements.

C. Variable Speculum Barrel Assembly

Figure 17:
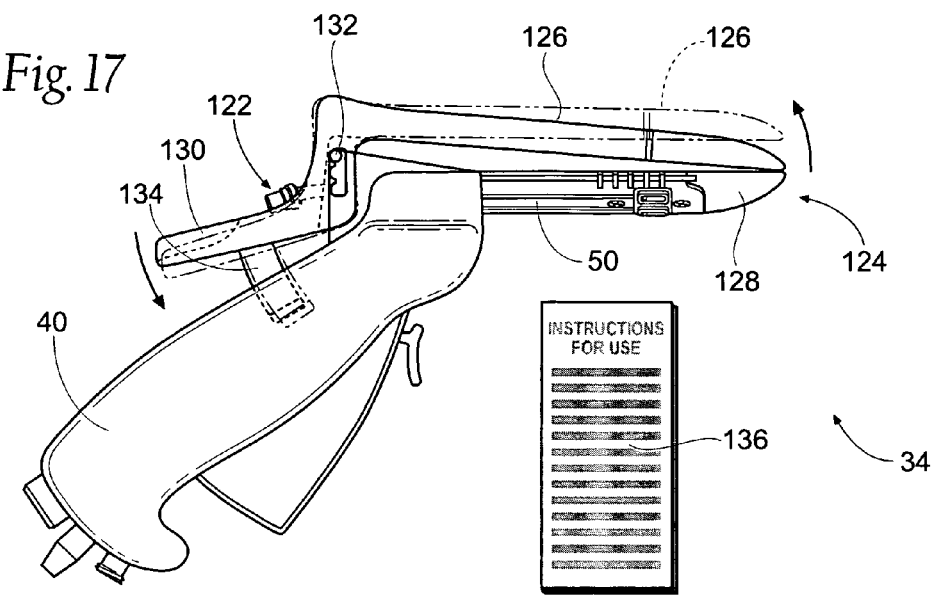
FIGS. 17 and 18 show a treatment device for treating sphincters and adjoining tissue regions in the rectum and anal canal, the treatment device comprising a variable speculum barrel assembly that is configured to adapt to the anatomic form and structure of different individuals in these tissue regions.
Figure 18:
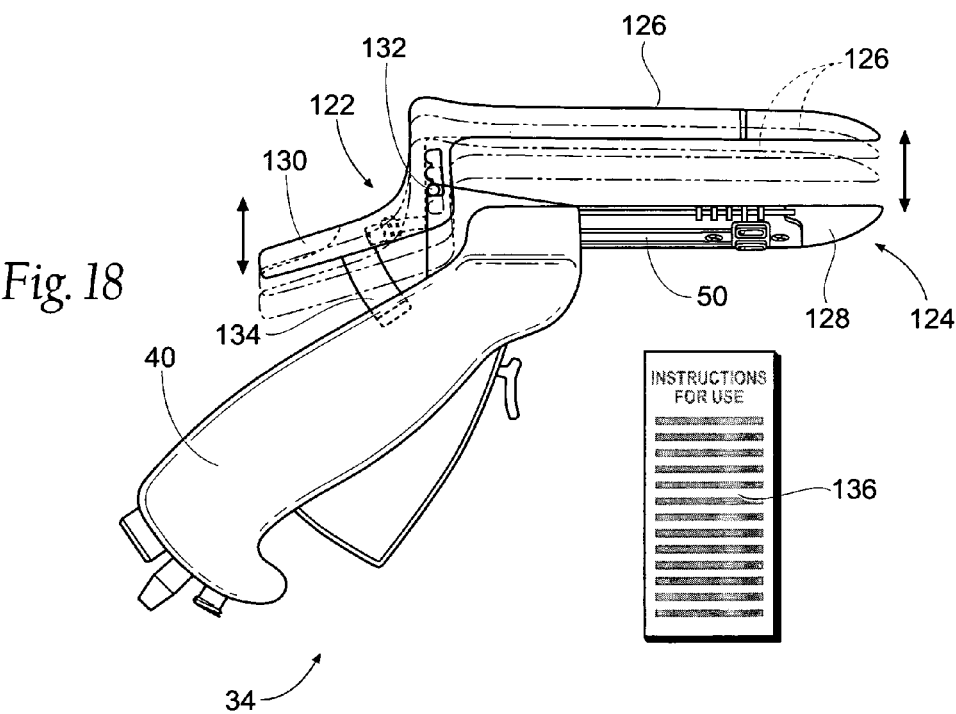

Alternatively, as shown in FIGS. 17 and 18, a treatment device 122 can comprise a handle grip 40 having a variable speculum barrel assembly 124. The variable speculum barrel assembly 124 includes upper and lower jaw components 126 and 128. The lower jaw component 128 is permanently coupled to the handle grip 40. The lower jaw component supports the carrier 50 and its components, which are secured within the lower jaw component 128 in the same manner already described.

The upper jaw component 126 is pivotally connected to the handle grip 40 for articulation relative to the lower jaw component 128. The upper jaw component 126 includes a handle 130 that articulates the upper jaw component 126 about a pivot point mount 132 with respect to the lower jaw component 128, which is fixed and coupled to the handle grip 40.

In this arrangement, the maximum outside diameter of the barrel assembly 124 is determined by degree of articulation of the upper jaw component 126 relative to the fixed lower jaw component 128. By articulation of the upper jaw component 126 (as shown in solid and phantom lines in FIG. 17), the system 34 can instantaneously provide a variable range of maximum outside diameters for the barrel assembly 124, from smallest, intermediate, to largest.

If desired (as FIGS. 17 and 18 show), the pivot point mount 132 can allow adjustment of the upper jaw component 126 in an up and down direction relative to the fixed lower jaw component 128. In this way, the range of maximum outside diameters for the barrel assembly 124 is variable. A frictional latch mechanism 134 can be provided to lock movement of the upper jaw component 126 when the articulation achieves a desired dimension.

The treatment device 122 can be packaged as a single use item in a sterile fashion within peripherally sealed sheets of plastic film material that are torn or peeled away at the instance of use. The system 34 can include, together with the particular treatment device 122 or separately supplied, instructions 136 for using the device 122. The instructions 136 for use can include the step of assessing the anatomic requirements of the individual to be treated, and adjusting the articulation of the upper jaw component 126 based upon the assessed anatomic requirements.

Features of the invention are set forth in the following claims.

We claim:

1. A method for forming a lesion in a targeted tissue region at or near a sphincter in the anal canal of an individual comprising
    assessing the anatomic requirements of the individual in the region of the anal canal,
    providing a barrel structure having a dimension selected based upon the assessing that is conducive for advancement into the anal canal, the barrel structure carrying an electrode sized and configured to be coupled to a source of tissue ablation energy to be applied through the electrode to form a lesion, the barrel structure including a transparent side wall visualized by a direct line of sight from an end portion of the barrel structure,
    inserting the barrel structure at the selected dimension into the anal cavity with the electrode retracted within the barrel structure,
    visualizing by the direct line of sight through the transparent side wall of the barrel structure the dentate line and the targeted tissue region,
    while visualizing, aligning the electrode in a desired location in the targeted tissue region above the dentate line,
    advancing the electrode to penetrate tissue at or near a sphincter, and
    applying energy through the electrode to create a lesion in the sphincter.

2. A method according to claim 1
    wherein providing the barrel structure includes providing a family comprising at least two barrel structures each having a different dimension.

3. A method according to claim 1 wherein providing the barrel structure includes
    providing a handle component,
    providing a family comprising at least two barrel structures each sized and configured to be individually attached to the handle component and each having a different dimension, each barrel structure carrying an electrode sized and configured to be coupled to a source of tissue ablation energy to be applied through the electrode to form a lesion, each barrel structure including a transparent side wall visualized by a direct line of sight from an end portion of the barrel structure,
    selecting one of the barrel structure based upon the assessing, and
    coupling the selected barrel structure to the handle component.

* * * * *